US008075823B2

(12) United States Patent
Guggenbichler et al.

(10) Patent No.: US 8,075,823 B2
(45) Date of Patent: Dec. 13, 2011

(54) PROCESS FOR PREPARING ANTIMICROBIAL PLASTIC BODIES HAVING IMPROVED LONG-TIME PERFORMANCE

(76) Inventors: J. Peter Guggenbichler, Munich (DE); Andreas Hirsch, Rathsberg (DE)

(*) Notice: Subject to any disclaimer, the term of this patent is extended or adjusted under 35 U.S.C. 154(b) by 6 days.

(21) Appl. No.: 11/789,232

(22) Filed: Apr. 24, 2007

(65) Prior Publication Data

US 2007/0194483 A1 Aug. 23, 2007

Related U.S. Application Data

(63) Continuation of application No. 10/060,835, filed on Jan. 30, 2002, now abandoned.

(30) Foreign Application Priority Data

Jul. 30, 1999 (DE) .................................. 199 36 059
Jul. 28, 2000 (DE) ....................... PCT/DE00/02493

(51) Int. Cl.
    *B29C 47/00* (2006.01)
(52) U.S. Cl. ................. 264/176.1; 264/211; 264/328.1; 264/319; 427/2.1; 427/2.24; 427/2.3; 427/2.31; 424/421; 424/618
(58) Field of Classification Search .................. 264/129, 264/131; 424/421, 618; 427/2.1, 2.24, 2.3, 427/2.31
    See application file for complete search history.

(56) References Cited

U.S. PATENT DOCUMENTS

| | | | | |
|---|---|---|---|---|
| 2,806,798 A | * | 9/1957 | Weaver | 106/1.18 |
| 2,809,798 A | | 9/1957 | Weaver | |
| 4,054,139 A | | 10/1977 | Crossley | |
| 4,677,143 A | | 6/1987 | Laurin et al. | |
| 4,851,081 A | * | 7/1989 | Forschirm | 216/83 |
| 5,019,096 A | | 5/1991 | Fox, Jr. et al. | |
| 5,063,179 A | * | 11/1991 | Menashi et al. | 501/12 |
| 5,180,585 A | * | 1/1993 | Jacobson et al. | 424/405 |
| 5,236,649 A | | 8/1993 | Hall et al. | |
| 5,418,056 A | | 5/1995 | Noguchi et al. | |
| 5,476,881 A | | 12/1995 | Suh | |
| 5,503,840 A | * | 4/1996 | Jacobson et al. | 424/421 |
| 5,516,480 A | | 5/1996 | Krall et al. | |
| 5,538,766 A | | 7/1996 | Banks et al. | |
| 5,662,913 A | | 9/1997 | Capelli | |
| 5,824,267 A | * | 10/1998 | Kawasumi et al. | 422/28 |
| 5,837,275 A | | 11/1998 | Burrell et al. | |
| 5,976,562 A | * | 11/1999 | Krall et al. | 424/402 |
| 6,544,536 B1 | | 4/2003 | Krall et al. | |
| 6,720,006 B2 | | 4/2004 | Hanke et al. | |
| 6,822,034 B2 | | 11/2004 | Hanke et al. | |
| 2005/0130163 A1 | | 6/2005 | Smith et al. | |

FOREIGN PATENT DOCUMENTS

| | | |
|---|---|---|
| CA | 2380490 | 2/2001 |
| DE | 2217399 | 11/1972 |
| DE | 3837125 | 5/1990 |
| DE | 3942112 | 6/1991 |
| DE | 4402890 | 8/1995 |
| DE | 19640364 | 4/1998 |
| DE | 19756790 | 7/1999 |
| DE | 19936059 | 2/2001 |
| DE | 10013248 | 9/2001 |
| EP | 0190504 A2 | 8/1986 |
| EP | 0318196 A2 | 5/1989 |
| EP | 0427858 | 9/1990 |
| EP | 0433961 | 6/1991 |
| EP | 0251783 | 4/1993 |
| EP | 0550875 | 7/1993 |
| EP | 0695501 | 8/1994 |
| EP | 0711113 B1 | 7/1997 |
| JP | 2-298517 | 2/1990 |
| JP | 03045709 A | 2/1991 |
| JP | 03-122162 | 5/1991 |
| JP | 04-231062 | 8/1992 |
| JP | 4243908 | 9/1992 |
| JP | 6-256563 | 6/1994 |
| JP | 07033617 | 2/1995 |
| JP | 07033906 A * | 2/1995 |
| JP | 07097767 A | 4/1995 |
| JP | 07238001 A * | 9/1995 |
| JP | 8-127700 | 8/1996 |
| JP | 11-172154 | 6/1999 |
| JP | 11169724 | 6/1999 |
| JP | 11172154 A | 6/1999 |
| WO | WO87/03495 | 6/1987 |
| WO | WO89/04682 | 6/1989 |
| WO | WO93/23092 | 11/1993 |
| WO | WO94/04202 | 3/1994 |
| WO | WO 94/15462 | 7/1994 |
| WO | WO 94/15463 | 7/1994 |
| WO | WO95/20878 | 8/1995 |
| WO | WO98/31404 | 7/1998 |

OTHER PUBLICATIONS

Mosby's Dental Dictionary, 2008, definition of "colloid".*
Translation of Ichikawa, JP 01222162.*
"Colloid," The Hutchinson Unabridged Encyclopedia with Atlas and Weather guide, 2009.*
Patent abstracts of Japan for Japanese Patent Publication No. 06-016509 and computer translation of patent (5 pgs).

(Continued)

*Primary Examiner* — Jennifer K. Michener
*Assistant Examiner* — Magali P. Slawski
(74) *Attorney, Agent, or Firm* — Kagan Binder, PLLC

(57) ABSTRACT

The present invention relates to processes for preparing an antimicrobial plastic body, said processes comprising molding a precursor and being characterized in that prior to molding at least one component of the precursor is treated with a metal colloid.

20 Claims, No Drawings

OTHER PUBLICATIONS

Patent abstracts of Japan for Japanese Patent Publication No. 06-0165 and computer translation of patent (5 pgs).
Pal, et al, "Use of a Silver—Gelatin Complex for the Determination of Micro-amounts of Hydrazine in Water," Analyst, vol. 111, Dec. 1986, pp. 1413, 1415.
Abstract of DE 19640364, Apr. 2, 1998, 1 pg.
Derwent Abstract of JP-336294, Jul. 1, 1992, 1 pg.
CRC Handbook of Chemistry and Physics, 61, Auflage, 1980 to 1981, p. F-98.
Abstract of JP03-122162, May 24, 1991, p. 1.
Abstract of JP04-231062, Aug. 19, 1992. p. 1.
Abstract of JP11-172154, Jun. 29, 1999, pp. 1-9.

* cited by examiner

PROCESS FOR PREPARING ANTIMICROBIAL PLASTIC BODIES HAVING IMPROVED LONG-TIME PERFORMANCE

PRIORITY CLAIM

The present Continuation patent application claims the benefit of U.S. National Stage patent application Ser. No. 10/060,835, filed Jan. 30, 2002, entitled PROCESS FOR PREPARING ANTIMICROBIAL PLASTIC BODIES HAVING IMPROVED LONG-TIME PERFORMANCE, which claims the benefit of International Application No. PCT/DE00/02493, filed on Jul. 28, 2000, and having a PCT Publication No. WO 01/09229, entitled PROCESS FOR PREPARING ANTIMICROBIAL PLASTIC BODIES HAVING IMPROVED LONG-TIME PERFORMANCE, and also claims priority from DE 199 36 059.6, which was filed on Jul. 30, 1999, wherein all prior patent applications are commonly owned by the owner of the present patent application and wherein the entireties for all purposes of said applications and prior patent applications are incorporated herein by reference.

FIELD OF THE INVENTION

The invention relates to processes for preparing antimicrobial metal-containing plastic bodies, in particular articles for medical requirements. These articles are in particular used in the form of catheters.

A considerable disadvantage of plastic articles for medical requirements, in particular of catheters for long-term and short-term use, is that the plastics used are easily infected by germs which are often multi-resistant and form a biofilm on the surface of the plastic body or on the outer and interior surface of the catheter. Prophylactic impregnation of the surfaces by means of antibiotics has to be ruled out due to the high selection of resistant microorganisms involved.

Thus, in the past years numerous attempts have been made to impregnate the plastic surfaces with silver ions originating from, e.g., silver nitrate, acetate or chloride. Among all heavy metal ions, silver ions have a very broad antimicrobial spectrum and high toxicity towards microorganisms in that they, e.g., bind to the cell wall via SH groups, block the respiratory chain, stop cell proliferation via DNA binding, but have low toxicity towards animal cells. In this context, however, sufficient microbial activity could not be observed in various clinical studies. Moreover, the etching effect and the poor water solubility, respectively, of silver salts cause further problems in use.

When metal surfaces such as silver are contacted with physiological NaCl solution, metal ions (silver ions) will be released depending on the size of the metal surface. Admixing a polymer such as polyurethane with a metal powder such as silver powder, however, will not be successful since due to the small surface area relatively high concentrations of metal powder will be necessary, which causes mechanical problems in the plastic material. The critical surface area required for antimicrobial activity, thus, cannot be obtained by admixing metal powder.

EP-A-0 711 113 discloses a new technology in which metallic silver is vapor deposited on polyurethane films which are compounded in comminuted form. This made it possible to achieve uniform distribution of silver particles in polymer material and, thus, obtain a surface area sufficiently large for bacteriostatic activity. The antimicrobial activity of said plastic bodies has been very well established as regards reduction and prevention of adherence, biofilm formation and long-time performance as well as toxicity and compatibility. The applicability of the aforesaid plastic bodies is, however, limited due to the time-consuming and costly preparation process, in particular caused by the vapor deposition of silver.

U.S. Pat. No. 5,180,585 furthermore describes an antimicrobial composition comprising inorganic particles having a first microbicidal layer and a second layer which protects the underlying first layer. The preparation process is relatively complex.

Thus, the object underlying the present invention is to provide a process for preparing antimicrobially active plastic bodies which do not exhibit the aforesaid disadvantages, i.e. can easily be prepared and provide sufficient concentration of silver ions at the surface.

This problem is solved by means of a process which is characterized in that prior to molding the plastic body at least one component of the precursor of the molded article is treated with a silver colloid.

Many polymer compounds commonly used in the medical field can be used as the starting material for the plastic body. Among these are in particular polyethylene, polypropylene, crosslinked polysiloxanes, polyurethanes, (meth)acrylate-based polymers, cellulose and cellulose derivatives, polycarbonates, ABS, tetrafluoroethylene polymers, and polyethylene terephthalates as well as the corresponding copolymers. Polyurethane, polyethylene and polypropylene as well as polyethylene-polypropylene copolymers are particularly preferred. The metal used is preferably silver, copper, gold, zinc or cerium. Among these metals, silver is particularly preferred.

Apart from colloidal metal, one or several polymer materials are used in the preparation of the plastic bodies according to the invention. Further additives can also be added to the mixture of colloidal metal and plastic(s). These are, in particular, inorganic particles such as barium sulfate, calcium sulfate, strontium sulfate, titanium oxide, aluminium oxide, silicon oxide, zeolites, mica, talcum, kaolin etc. In this context, barium sulfate which can simultaneously act as a X-ray contrast medium for specific fields of application is particularly preferred.

Prior to molding, one or several polymer components and/or one or several of the inorganic additives are treated with the colloidal metal solution.

After mixing of the starting materials which have (in part) been treated with a colloidal metal, the resulting mixture is further processed in order to obtain a molded plastic article. This can be done in mixers, kneaders, extruders, injection molding machines or (hot) presses.

The metal colloids with which the plastic materials or inorganic particles are treated are suitably prepared by reducing metal salt solutions. In order to stabilize the resulting colloid, protective agents such as gelatin, silica or starch may be used.

In one embodiment of the present invention, a preferred metal silver colloid is prepared by slowly blending an ammoniacal silver nitrate solution in gelatin with a suitable reducing agent. The reducing agent preferably is selected from aldehydes (e.g. acetaldehyde), aldoses (e.g. glucose), quinones (e.g. hydroquinone), inorganic complex hydrides (sodium or potassium boranate), reducing nitrogen compounds (hydrazine, polyethylene imine) and ascorbic acid.

Plastic precursors such as pellets and/or said inorganic particles such as barium sulfate are then treated with said colloidal silver solution, dried and molded into the respective shape. Applying said silver colloid onto the starting materials and subsequent drying can be repeated several times so that in this way very high silver concentrations can be introduced into the plastic material. This is of particular advantage if barium sulfate is coated with silver since in this way the plastic pellets do not necessarily have to be coated in advance.

The suspension can also be freed from solvent by filtration and it can subsequently be freed from all low-molecular organic compounds by first washing it with about 5% ammonia solution and then several times with distilled water. As described above, after drying in air the filter residue will give a homogeneous material. This process can also be repeated several times.

The use of e.g. gelatin, (fumed) silica or starch as a colloidal stabilizer can be omitted if silver is adsorbed by the inorganic particles, since the microcrystalline silver particles produced during reduction bind to the surface of said inorganic particles via adsorption and, thus, the formation of a continuous silver coating on the solid is avoided. Water soluble adjuvant chemicals used can be removed with water.

By varying or omitting the colloidal stabilizers as well as the reducing agents, the particle size of the silver and, thus, the mobility of the resulting silver ions can be controlled over a wide range and, moreover, by using low-molecular aldehydes as the reducing agents which partially crosslink gelatin, very strong adhesion to the polymer can be achieved.

In the following, the process according to the invention will be exemplified by way of examples.

EXAMPLE 1

Preparation of the Silver Colloid 1.0 g gelatin (DAB) are dissolved in 100 ml distilled water at 40° C. whilst stirring. Subsequently, 1.0 g (5.88 mmol) $AgNO_3$ p.a. are added thereto and the resulting solution is blended with 1.0 ml (14.71 mmol) water containing 25% $NH_3$.

For the preparation of the silver colloid, 258.7 mg (5.88 mmol, 330 µl) acetaldehyde, dissolved in 50 ml distilled water, are slowly dripped into the above solution at 40° C. over a period of time of 30 min.

EXAMPLE 2

Coating of Polyurethane Pellets 10 min after the dripping according to Example 1 has been stopped, about 50 mg polyurethane pellets made of Tecothane TT-1085A are added and first vigorously stirred for 2 h at 40° C. and then for 3 h at room temperature so that they are coated with colloidal silver.

The silver colloid is separated by rapid filtration over a folded filter of a suitable pore size, the pellets are once again washed with the filtrate and the still wet pellets are transferred into a evaporating dish. After superfluous silver colloid solution which does not adhere to the polymer has been removed, the resulting product is dried for 10 h at 70° C.

EXAMPLE 3

Adsorption of Colloidal Silver on Barium Sulfate a) 0.666 g gelatin and then 6.66 g $AgNO_3$ are subsequently dissolved in 500 ml distilled water at 50° C. About 8.5 ml 25% aqueous $NH_3$ solution are added until the reaction is slightly alkaline.

A solution of 3.53 g anhydrous α-D-glucose in 150 ml distilled water is slowly dripped in at 50° C. whilst stirring vigorously and as soon as about half of the glucose solution has been dripped in, the resultant silver colloid is blended with 333 g $BaSO_4$. After the dripping has been stopped, the suspension is further turbinated for about 2 h at 50° C. and then freed from its volatile components by evaporation and drying at 70° C. The material is comminuted in a hand-held mortar.

b) The procedure is analogous to Example 3a), with the exception that 6.66 g fumed silica (Degussa, Aerosil 200) are used instead of gelatin. The particle size of the colloidal silver was in the range of from 10 to 50 nm, as determined via a scanning electron micrograph.

EXAMPLE 4

Alternative Adsorption of Colloidal Silver on Barium Sulfate

The procedure is analogous to Example 3a), with the exception that 1.2 l distilled water, 2 g gelatin, 20 g $AgNO_3$ and 26 ml 25% $NH_3$ solution are used. As the reducing agent, a solution of 10.59 g glucose in 400 ml distilled water is used and blended with 333 g $BaSO_4$ in analogy with Example 3a). The suspension is then further turbinated for 3 h at 50° C. and kept for about 8 h at 70° C. until the reaction is complete. The Ag-colloid adsorbed on $BaSO_4$ is freed from water and the components soluble therein (gelatin, gluconic acid, $NH_4NO_3$ and $NH_3$) by filtering the suspension which still should be as warm as possible and subsequently washing the residue four times with distilled water. Drying takes place at 70° C. and comminution is effected as in Example 3a).

The residual amount of organic material (gelatin, gluconic acid, glucose) of the material obtained according to Example 4 was determined by means of two independent methods with the proviso that under the conditions used gelatin and gluconic acid have comparable solubility in water.

By Combustion Analysis:

In this context the C and H values are below the measuring tolerance indicated by the manufacturer of the apparatus of 0.3%, i.e. with a finished compounded polyurethane material comprising 20% $BaSO_4$ and 0.8% Ag, the total amount of organic residues can be calculated to be theoretically at most 0.182 wt % (lowest value that can be detected by the apparatus). Thus, the actual value should be considerably lower.

By Thermogravimetry:

When comparing the material obtained according to Example 4 with a reference sample prepared in an identical way, but not washed (weight loss about 3.2%) and pure $BaSO_4$, a total weight loss of at most 0.28 wt % (gelatin: 0.045 wt %, gluconic acid: 0.235 wt %) or better can be observed. Thus, the finished compounded polyurethane comprising 20% $BaSO_4$ and 0.8% Ag exhibits a total content of organic residues of <0.056 wt % (gelatin: <0.009 wt %, gluconic acid: <0.047 wt %). Due to its considerably higher sensitivity, thermogravimetry is preferable over combustion analysis.

EXAMPLE 5

Determination of Antibacterial Activity

In order to determine whether the plastic bodies according to the invention can be infected with germs, five cylindrical samples each of the respective plastic (diameter 3 mm, length 13 mm) were incubated with a composition containing *Staphylococcus epidermis* in a Trypcase-Soy-Broth nutrient solution at 175° C. The following plastic bodies were examined (no. 1 is commercially available and untreated, nos. 2 and 3 are according to the invention):

Specimen 1: section taken from a PU catheter obtained from the company Arrow (ES 04701)

Specimen 2: according to Example 2 of the present invention

Specimen 3: according to Example 3 of the present invention.

The 5 specimens were each subjected to four test sequences under the following conditions:

Test sequence 1: initial concentration of *Staphylococcus epidermis* $5\times10^7$ CFU/ml Test sequence 2: initial concentration of *Staphylococcus epidermis* $10^8$ CFU/ml Test sequence 3: as in test sequence 1, but measured in physiological buffer solution at 37° C. after previous incubation for 5 hours.

Test sequence 4: as in test sequence 1, the plastic bodies having been treated with natural urine filtered to be sterile at 37° C. for 4 hours.

Table 1 shows the number of infected plastic bodies which was determined by visual control.

TABLE 1

|  | Specimen Type | Number of infected specimens | | | |
| --- | --- | --- | --- | --- | --- |
|  |  | Test Sequence 1 | Test Sequence 2 | Test Sequence 3 | Test Sequence 4 |
| Comparison | 1 | 3 | 5 | 4 | 5 |
| Invention | 2 | 0 | 0 | 0 | 0 |
|  | 3 | 0 | 3 | 0 | 0 |

After compounding, the catheter materials are not impaired in their mechanical properties required for therapeutical purposes (roughness, homogeneity and elasticity). The process can easily be adapted to varying requirements in the production process, since antimicrobial activity is maintained irrespective of whether the silver is introduced into the polymer material by coating the polyurethane pellets (Example 2) or via the X-ray contrast medium (Examples 3 and 4).

The plastic articles according to the invention show significantly higher antimicrobial activity with respect to adherence and biofilm formation as well as considerably improved long-time performance as compared with prior art materials at comparably lower toxicity.

The preparation processes according to the invention can easily be controlled, are economical and suited for large scale production. Example 4 additionally provides a process for removing all "adjuvant chemicals" from the inorganic contrast medium so that the grant of a protective certificate on the process should be possible.

EXAMPLE 6

Dependence of Antimicrobial Activity on Time

Catheters (the Amounts are Based on the Finished Compounded Material):
1) polyurethane catheters 20% $BaSO_4$+0.8% Ag, length 1.0 cm (Example 4)
2a) silicone catheters 25% $BaSO_4$+1% Ag, length 1 cm, thickness 1.3 mm and width 2 mm (Example 4)
2b) silicone catheters 25% $BaSO_4$+0.33% Ag+0.33% $SiO_2$ (Example 3b) silicone wall sections, length 1 cm, thickness 1 mm and width 2 mm
3) control Argen Tec 1 lumen catheter (Sicuris) Extr. 1/99 20% $BaSO_4$+0.9-1% Ag Sterilization: Storage in a hot-air cabinet at 90° C. for 3 hours. Previous tests showed that after this period of time the samples are free of germs. (even before that time samples are largely not infected with germs)

Germs: *S. epidermidis* (ref.: Infection Suppl. 6/99)
*E. coli*

Nutrient medium: Trypcase Soja

Way of proceeding:
samples are incubated with $5\times10^7$ germs at room temperature in a suspension of 0.45% NaCl with 2.5% glucose for 8 hours
the germ suspension is subsequently removed by centrifugation
washing two times (2 min of renewed suspension in physiological sodium chloride solution whilst swiveling)
transferring the samples into sterile sodium chloride solution in a Petri dish
sampling every hour, after 6 hours every 2 hours and transferring the samples into Trypcase Soja Medium after slight swiveling in physiological sodium chloride solution
incubation for 24 to 36 hours
evaluation of the sample for sterility (turbidity=measurement of the end point).

Results of tests with *S. epidermidis*

All samples are tested five times (+++++)

| Time: H | Sample 1 | Sample 2a | Sample 2b | Control |
| --- | --- | --- | --- | --- |
| 0 | +++++ | +++++ | +++++ | +++++ |
| 1 | +++++ | +++++ | +++++ | +++++ |
| 2 | +++++ | +++++ | +++++ | +++++ |
| 3 | ++++− | ++++− | +++++ | +++++ |
| 4 | ++++− | ++++− | +++++ | +++++ |
| 5 | ++−−− | ++−−− | ++++− | +++++ |
| 6 | −−−−− | +−−−− | ++−−− | +++++ |
| 8 | −−−−− | −−−−− | −−−−− | +++++ |
| 10 | −−−−− | −−−−− | −−−−− | +++++ |
| 12 | −−−−− | −−−−− | −−−−− | ++++− |
| 16 | −−−−− | −−−−− | −−−−− | +++−− |
| 18 | −−−−− | −−−−− | −−−−− | +++−− |

+ = broth turbid after 36 hours
− = broth clear (sterile) after 36 hours

Discussion:

In this test the antimicrobial activity of solids depending on time could be examined. It is shown that silver-filled samples exhibit antimicrobial activity already after 6 hours and a contaminated catheter can be made sterile again within this period of time even at a unphysiologically high inoculum. Lower Ag concentration as in sample 2b will also have a positive result.

Results of Tests with *E. coli*

All samples are tested five times (+++++)

| Time: H | Sample 1 | Sample 2a | Sample 2b | Control |
| --- | --- | --- | --- | --- |
| 0 |  | +++++ | +++++ | +++++ |
| 1 |  | +++++ | +++++ | +++++ |
| 2 |  | +++++ | +++++ | +++++ |
| 3 | ++++− | +++++ | +++++ | +++++ |
| 4 | ++++− | +++++ | +++++ | +++++ |
| 5 | ++++− | ++++− | ++++− | +++++ |

-continued

| Time: H | Sample 1 | Sample 2a | Sample 2b | Control |
|---|---|---|---|---|
| 6  |       | +++--  | ++++-  | +++++ |
| 8  |       | ++---  | +++--  | +++++ |
| 10 |       | +----  | +----  | +++++ |
| 12 |       | -----  | -----  | +++++ |
| 16 |       | -----  | -----  | ++++- |
| 18 |       | -----  | -----  | ++++- |

The results for *S. epidermidis* are equally good even after the silver has been eluted in physiological NaCl solution for 1, 2 and 3 weeks and the results are identical to those in Table 1.

The examination for cytotoxicity was carried out by the company Toxikon, Bedford Mass., USA. It was shown that the samples prepared are not toxic and fulfil the requirements of the elution test ISO 10993.

The invention claimed is:

1. A process for preparing an antimicrobial plastic body comprising colloidal metal, one or several polymer materials and one or several inorganic additives, said process comprising the steps of
    (A) preparing a metal colloid solution comprising colloidal metal and organic stability protective agent, wherein the colloidal metal consists of metal particles,
    (B) treating at least one of the one or several inorganic additives with the metal colloid solution to form a suspension,
    (C) removing organic stability protective agent from the suspension of step B) to obtain a solid, drying the solid, and adding the one or several polymer materials to obtain a precursor, and
    (D) molding the precursor obtained in step (C) to form the antimicrobial plastic body.

2. The process as claimed in claim 1 wherein the one or several polymer materials includes polyurethane.

3. The process as claimed in claim 1 wherein several inorganic additives are treated with the metal colloid solution to form the suspension.

4. The process as claimed in claim 1 wherein said inorganic additives comprise barium sulfate, calcium sulfate, strontium sulfate, titanium oxide, aluminum oxide, silicon oxide, zeolites, mica, talcum or kaolin.

5. The process as claimed in claim 1 wherein additionally at least one of the one or several polymer materials are treated with the metal colloid solution.

6. The process as claimed in claim 1 wherein the colloidal metal is colloidal silver.

7. The process as claimed in claim 1 wherein removing organic stability protective agent from the suspension of step (B) comprises filtering the suspension.

8. The process as claimed in claim 1 wherein after adding the one or several polymer materials in step (C), the amount of organic stability protective agent in the precursor is less than 0.182 wt %.

9. The process as claimed in claim 1 wherein after adding the one or several polymer materials in step (C), the amount of organic stability protective agent in the precursor is less than 0.056 wt %.

10. The process as claimed in claim 1 wherein molding the precursor in step (D) comprises mixing, kneading, extruding, injection molding or hot press molding.

11. The process as claimed in claim 1 wherein the organic protective agent is gelatin or starch.

12. The process as claimed in claim 1 wherein the antimicrobial plastic body is a medical device.

13. The process as claimed in claim 12 wherein the antimicrobial plastic body is a catheter.

14. A process for preparing an antimicrobial plastic body comprising colloidal metal, one or several polymer materials and one or several inorganic additives, said process comprising the steps of
    (A) preparing a metal colloid solution comprising colloidal metal and organic stability protective agent, wherein the colloidal metal consists of metal particles,
    (B) treating at least one of the one or several polymer materials with the metal colloid solution to form a suspension,
    (C) removing organic stability protective agent from the suspension of step B) to obtain a solid, drying the solid, and adding the one or several inorganic additives to obtain a precursor, and
    (D) molding the precursor obtained in step (C) to form the antimicrobial plastic body.

15. The process as claimed in claim 14 wherein the one or several polymer materials includes polyurethane.

16. The process as claimed in claim 14 wherein said inorganic additives comprise barium sulfate, calcium sulfate, strontium sulfate, titanium oxide, aluminum oxide, silicon oxide, zeolites, mica, talcum or kaolin.

17. The process as claimed in claim 14 wherein additionally at least one of the one or several inorganic additives are treated with the metal colloid solution.

18. The process as claimed in claim 14 wherein the colloidal metal is colloidal silver.

19. The process as claimed in claim 14 wherein the antimicrobial plastic body is a medical device.

20. The process as claimed in claim 19 wherein the antimicrobial plastic body is a catheter.

* * * * *